(12) United States Patent
Lieberman et al.

(10) Patent No.: US 11,574,701 B1
(45) Date of Patent: Feb. 7, 2023

(54) COMPUTING SYSTEM FOR NORMALIZING COMPUTER-READABLE GENETIC TEST RESULTS FROM NUMEROUS DIFFERENT SOURCES

(71) Applicant: Allscripts Software, LLC, Raleigh, NC (US)

(72) Inventors: Yuval Lieberman, Nevatim (IL); Peter DeVries, Chicago, IL (US); Dan Alon, Beer-Sheva (IL); Scott Sumner, Westlake, CA (US)

(73) Assignee: ALLSCRIPTS SOFTWARE, LLC, Raleigh, NC (US)

( * ) Notice: Subject to any disclaimer, the term of this patent is extended or adjusted under 35 U.S.C. 154(b) by 821 days.

(21) Appl. No.: 16/203,040

(22) Filed: Nov. 28, 2018

(51) Int. Cl.
| | |
|---|---|
| *G16B 20/00* | (2019.01) |
| *G16H 10/40* | (2018.01) |
| *G16B 50/00* | (2019.01) |
| *G16H 10/60* | (2018.01) |
| *G16B 30/00* | (2019.01) |

(52) U.S. Cl.
CPC ............. *G16B 20/00* (2019.02); *G16B 50/00* (2019.02); *G16H 10/40* (2018.01); *G16B 30/00* (2019.02); *G16H 10/60* (2018.01)

(58) Field of Classification Search
None
See application file for complete search history.

(56) References Cited

U.S. PATENT DOCUMENTS

| 7,788,040 B2 | 8/2010 | Haskell et al. |
| 2010/0121872 A1 | 5/2010 | Subramaniam |
| 2014/0350968 A1 | 11/2014 | Hahn et al. |

FOREIGN PATENT DOCUMENTS

| CN | 1894698 A | 1/2007 |
| WO | 2012098515 A1 | 7/2012 |

OTHER PUBLICATIONS

"Lexical analysis," Wikipedia at https://en.wikipedia.org/wiki/Lexical_analysis, pages, as downloaded Aug. 28, 2021.*

* cited by examiner

*Primary Examiner* — G Steven Vanni
(74) *Attorney, Agent, or Firm* — Calfee, Halter & Griswold LLP

(57) ABSTRACT

A computer-executable application receives genetic test results for a genetic test a patient has undergone, an identifier for the genetic test, and an identifier for the genetic laboratory that performed the genetic test. The application identifies a format type of the genetic test results. When the format type is unstructured, the application performs an optical character recognition process to the genetic test results such that the format type of the genetic test results is semi-structured. When the format type is semi-structured, the application identifies a set of lexing and parsing rules assigned to the genetic test. The application generates processed genetic test results by applying the set of lexing and parsing rules to the genetic test results and stores the processed genetic test results in a data store. When the format type is structured, the application stores the genetic test results as the processed genetic test results in the data store.

12 Claims, 8 Drawing Sheets

Date of Birth: 9/20/70  Medical Facility: Hospital  Patient Name: John Doe
Sex: Male  Ordering Physician: Dr. Kim  Specimen Site: Lymph Node
Case Number: 123  Additional Recipient: None  Date of Collection: 10/08/18
Medical Record Number: 456    Specimen Type: Tissue
Specimen ID: 789  Pathologist: Dr. Jay

TUMOR TYPE: LUNG ADENOCARCINOMA

<u>Patient Results</u>

11 genomic findings
10 therapies associated with potential clinical benefit
0 therapies associated with lack of response
19 clinical trials <u>Genomic Alterations Identified</u>

*ERBB2* amplification – equivocal
*NF2* E427
*STK11* splice site 921-1G>C
*CDKN18* E105Fs*14
*FOXP1* E490*
*KDMSC* W983*
*LRP1B* loss exons 6-14
*SPTA1* Q1346fs*3, splice site 3570-2A>T
*TP53* I255S <u>Additional Disease-relevant genes with no Reportable Alterations Identified</u>

*EGFR*
*KRAS*
*ALK*
*BRAF*
*MET*
*RET*
*ROS1*

<u>Additional Findings</u>

*Tumor Mutation Burden* TMB-High; 37.53 Muts/Mb

FIG. 3

COMPUTING SYSTEM FOR NORMALIZING COMPUTER-READABLE GENETIC TEST RESULTS FROM NUMEROUS DIFFERENT SOURCES

BACKGROUND

Genetic tests for genetic conditions are increasingly used by healthcare providers in deciding how to best treat patients. Genetic test results for a genetic test of a patient typically include identifiers for a genetic condition tested for by the genetic test, identifiers for genes (and variations of genes) associated with the genetic test, and an indication of whether the patient has the genetic condition. Genetic test results for genetic tests typically are provided to computing systems of healthcare providers by genetic laboratories in an unstructured format, a semi-structured format, or a structured format.

Genetic test results formatted in an unstructured format do not include computer-readable text and hence are not searchable by a computing device. An example of an unstructured format is an image file format, such as a Joint Photographic Experts Group (JPEG) file.

Genetic test results formatted in a semi-structured format include computer-readable text and hence are searchable by a computing device. However, different semi-structured genetic test results may employ different labels for the same data elements. For instance, first semi-structured genetic test results from a first genetic laboratory may refer to a genetic variation as a "genetic variation," while second semi-structured genetic test results from a second genetic laboratory may refer to the (same) genetic variation as a "genetic alteration." An example of a semi-structured format is a searchable portable document format (PDF) file or a text file (.txt).

Genetic test results formatted in a structured format include computer-readable text, as well as standardized labels for data elements in the genetic test results. For instance, first structured genetic test results from a first genetic laboratory and second structured genetic test results from a second genetic laboratory both may both refer to a genetic variation as a "genetic variation." An example of structured genetic test results may be genetic test results that are stored according to a Clinical Document Architecture (CDA) standard.

Conventionally, genetic test results for genetic tests are stored in the computing systems of the healthcare providers in the same format in which they are received from a device of a genetic laboratory that performed the genetic test. This is undesirable for several reasons. First, file sizes of unstructured and semi-structured genetic test results may be large, and hence storing unstructured and semi-structured genetic test results may be burdensome on storage resources of the computing systems of the healthcare providers. Second, storing genetic test results in different formats is not conducive to performing population level analytics on the genetic test results. Third, genetic test results stored in an unstructured format are not searchable and do not have semantic annotation.

SUMMARY

The following is a brief summary of subject matter that is described in greater detail herein. This summary is not intended to be limiting as to the scope of the claims.

Disclosed herein are various technologies pertaining to ingesting genetic test results. More specifically, a genetic test results ingestion application is described herein. The genetic test results ingestion application is configured to process and store genetic test results that are received from a genetic laboratory device in an unstructured format, a semi-structured format, or a structured format.

In operation, the genetic test results ingestion application executes on a server computing device and receives genetic test results for a genetic test that a patient has undergone from a genetic laboratory device of a genetic laboratory that performed the genetic test. The genetic test results ingestion application also receives an identifier for the genetic laboratory and an identifier for the genetic test from the genetic laboratory device. In an embodiment, the identifier for the genetic laboratory and the identifier for the genetic test are comprised by the genetic test results. In another embodiment, the identifier for the genetic laboratory and the identifier for the genetic test are received separately from the genetic test results.

The genetic test results are formatted in an unstructured format, a semi-structured format, or a structured format. Genetic test results formatted in the unstructured format fail to include computer-readable text. Example unstructured formats include a non-searchable portable document format (PDF), a facsimile, or an image file format, such as a joint photographic experts group (JPEG), a JPEG file interchange format (JFIF), a tagged imaged file format (TIFF), a graphics interchange format (GIF), a windows bitmap (BMP), and/or a portable network graphics (PNG).

Genetic test results formatted in the semi-structured format include computer-readable text (and hence are searchable by a computing device), but fail to include standardized labels for data elements found in the (semi-structured) genetic test results. For instance, first semi-structured genetic test results may use the term "genetic disorder" to refer a health condition of a patient caused by one or more abnormalities in a genome of the patient, while second semi-structured genetic test results may use the term "genetic condition" instead. Example semi-structured formats include searchable PDFs, Hypertext Markup Language (HTML), text files (e.g., .txt), and document formats, such as .doc and .docx.

Genetic test results formatted in the structured format include computer-readable text and utilize standardized labels for data elements found in the (structured) genetic test results. Example structured formats include Health Level Seven International (HL7), clinical document architecture (CDA), consolidated clinical document architecture (CCDA), and comma-separated values (CSV).

The genetic test results ingestion application identifies whether the genetic test results are formatted in the unstructured format, the semi-structured format, or the structured format. For instance, the genetic test results ingestion application may read a file extension of the genetic test results and may identify the genetic test results as being formatted in the unstructured format, the semi-structured format, or the structured format based upon the file extension.

When the genetic test results ingestion application identifies the genetic test results as being formatted in the unstructured format, the genetic test results ingestion application applies an optical character recognition (OCR) process to the genetic test results such that the genetic test results are formatted in the semi-structured format. More specifically, the OCR process may read pixels in the (unstructured) genetic test results that are indicative of text and generate computer-readable text based upon the pixels. In an example, the OCR process may take a JPEG image of the genetic test results as input and output a searchable PDF or a text file (e.g., a file with a .txt file extension).

When the genetic test results ingestion application identifies the genetic test results as being formatted in the semi-structured format (either originally in the semi-structured format or in the semi-structured format as a result of the OCR process), the genetic test results ingestion application executes a search over sets of lexing and parsing rules retained in a data store accessible to the genetic test results ingestion application. Each set of lexing and parsing rules in the sets of lexing and parsing rules is assigned to a different genetic test performed by a different genetic laboratory. The search is based upon the identifier for the genetic test and the identifier for the genetic laboratory. The search produces search results, and the genetic test results ingestion application identifies a set of lexing and parsing rules assigned to the genetic test performed by the genetic laboratory based upon the search results. The genetic test results ingestion application then generates processed genetic test results for the genetic test results by applying the set of lexing and parsing rules to the (semi-structured) genetic test results. In an embodiment, the processed genetic test results are formatted in the structured format. The genetic test results ingestion application then stores the processed genetic test results for the patient in the data store (or another data store).

When the genetic test results ingestion application identifies the genetic test results as being formatted in the structured format, the genetic test results ingestion application stores the genetic test results in the data store as the processed genetic test results.

Subsequently, it is contemplated that a healthcare worker (e.g., a general practitioner, a cardiologist, a geneticist, etc.) wishes to view the processed genetic test results for the patient. As such, a client computing device operated by the healthcare worker receives input from the healthcare worker indicating an intent to view the processed genetic test results. The client computing device is in network communication with the server computing device and transmits an indication of the intent to view the processed genetic test results to the server computing device. Responsive to receiving the indication, the genetic test results ingestion application transmits the processed genetic test results to the client computing device, whereupon the client computing device presents the processed genetic test results on a display.

The above-described technologies present various advantages over conventional technologies for storing and processing genetic test results for patients. First, the above-described technologies increase efficiency of storing genetic test results in a data store as the genetic test results may be stored exclusively in a structured format. Second, the above-described technologies are more conducive to population-level genetic analytics due to storage of the genetic test results exclusively in a structured format.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF THE DRAWINGS

FIG. 3 is a depiction of exemplary semi-structured genetic test results for a patient.

DETAILED DESCRIPTION

Figure 1:
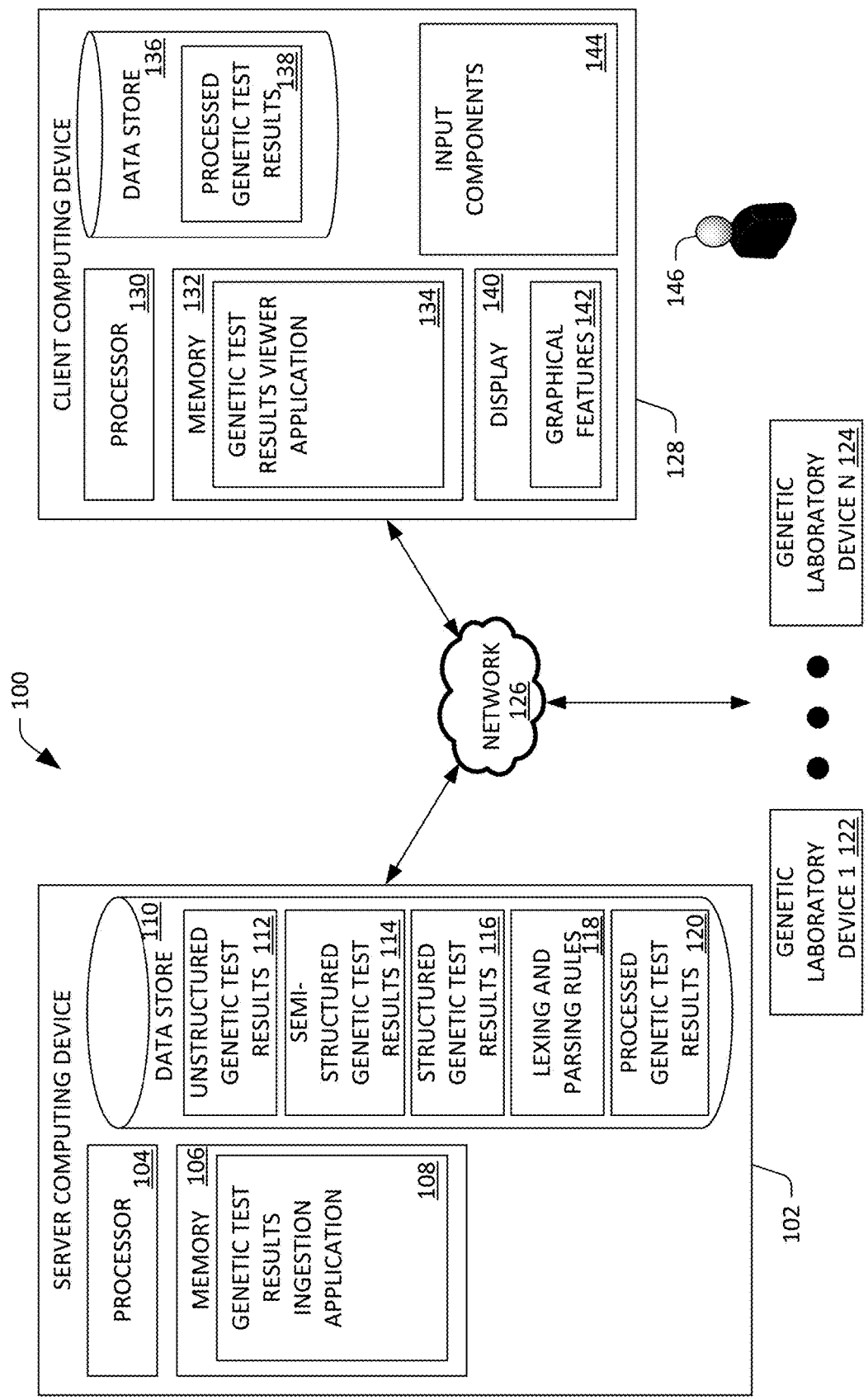
FIG. 1 is a functional block diagram of an exemplary computing system that facilitates ingesting genetic test results.

Various technologies pertaining to ingesting genetic test results for patients are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

With reference to FIG. 1, an exemplary computing system 100 that facilitates ingesting genetic test results is illustrated. The computing system 100 includes a server computing device 102. The server computing device 102 comprises a processor 104 and memory 106, wherein the memory 106 has a genetic test results ingestion application 108 loaded therein. As will be described in greater detail below, the genetic test results ingestion application 108 is configured to receive genetic test results in an unstructured format, a semi-structured format, or a structured format and store the genetic test results as processed genetic test results.

The server computing device 102 includes a data store 110. The data store 110 may retain genetic test results 112-116 for patients, sets of lexing and parsing rules 118 assigned to different genetic tests performed by different genetic laboratories, and processed genetic test results 120.

The genetic test results 112-116 may include unstructured genetic test results 112, semi-structured genetic test results 114, and structured genetic test results 116. Unstructured genetic test results 112 (i.e., genetic test results in an unstructured format) do not include computer-readable text and as such the unstructured genetic test results 112 are formatted in one or more unstructured formats. Example unstructured formats may include a non-searchable portable document format (PDF), a facsimile, or an image file, such as a joint photographic experts group (JPEG), a JPEG file interchange format (JFIF), a tagged imaged file format (TIFF), a graphics interchange format (GIF), a windows bitmap (BMP), and/or a portable network graphics (PNG). Semi-structured genetic test results 114 (i.e., genetic test results in a semi-structured format) include computer-readable text, but do not utilize standardized labels for data elements. As such, the semi-structured genetic test results 114 are formatted in one or more semi-structured formats. Example semi-structured formats may include searchable PDFs, Hypertext Markup Language (HTML), text files (e.g., .txt), and/or document formats, such as .doc and .docx. Structured genetic test results 116 (i.e., genetic test results in a structured format) include computer-readable text utilize standard labels for data elements. As such, the structured genetic test results 116 are formatted in one or more structured formats. Example structured formats may include Health Level Seven International (HL7), clinical document architecture (CDA), consolidated clinical document architecture (CCDA), and/or comma-separated values (CSV).

Each set of lexing and parsing rules in the sets of lexing and parsing rules 118 is assigned to a different genetic test performed by a different genetic laboratory. In an example, a first set of lexing and parsing rules in the sets of lexing and parsing rules 118 is assigned to a first genetic test performed by a first genetic laboratory and a second set of lexing and parsing rules in the sets of lexing and parsing rules 118 is assigned to a second genetic test performed by a second genetic laboratory. In another example, a third set of lexing and parsing rules in the sets of lexing and parsing rules 118 is assigned to the first genetic test performed by a third genetic laboratory. In yet another example, a fourth set of lexing and parsing rules in the sets of lexing and parsing rules 118 is assigned to a fourth genetic test performed by the first genetic laboratory. A set of lexing and parsing rules in the sets of lexing and parsing rules 118 may include a set of regular expressions. The set of regular expressions may refer to a sequence of computer-readable characters that define a search pattern. The genetic test results ingestion application 108 may apply the set of lexing and parsing rules to semi-structured genetic test results in order to generate processed genetic test results, wherein the processed genetic test results may be in a structured format.

The processed genetic test results 120 are genetic test results that are to be stored and utilized by the genetic test results ingestion application 108. For instance, the processed genetic test results 120 may be formatted in one of the structured formats identified above.

While the unstructured genetic test results 112, the semi-structured genetic test results 114, the structured genetic test results 116, the sets of lexing and parsing rules 118, and the processed genetic test results 120 are all depicted as being retained in the data store 110 of the server computing device 102, it is to be understood that some or all of the unstructured genetic test results 112, the semi-structured genetic test results 114, the structured genetic test results 116, the sets of lexing and parsing rules 118, and the processed genetic test results 120 may be retained in different data stores of different computing devices.

The genetic test results 112-116 are generated by a plurality of genetic laboratory devices 122-124. The plurality of genetic laboratory devices 122-124 may be operated by different genetic laboratories. In an embodiment, some or all of the plurality of genetic laboratory devise 122-124 are computing devices. In another embodiment, some or all of the plurality of genetic laboratory devise 122-124 are facsimile machines. The genetic laboratory devices 122-124 may be in communication with the server computing device 102 by way of a network 126 (e.g., the Internet, intranet, etc.).

The computing system 100 may additionally include a client computing device 128 operated by a healthcare worker 146 (e.g., a general practitioner, a cardiologist, a geneticist, etc.). In a non-limiting example, the client computing device 128 may be a desktop computing device, a laptop computing device, a tablet computing device, or a smartphone. The client computing device 128 is in communication with the server computing device 102 by way of the network 126 (or another network).

The client computing device 128 comprises a processor 130 and memory 132, wherein the memory 132 has a genetic test results viewer application 134 loaded therein. The genetic test results viewer application 134 is configured to present processed genetic test results for patients to the healthcare worker 146.

The client computing device 128 may include a data store 136 that retains processed genetic test results 138. It is understood that the processed genetic test results 138 may overlap in part or wholly with the genetic test results 120 retained in the data store 110 of the server computing device 102.

The client computing device 128 may include a display 140, whereupon graphical features 142 may be presented thereon. For instance, a graphical user interface (GUI) for the genetic test results viewer application 134 may be presented on the display 140 as part of the graphical features 142.

The client computing device 128 may include input components 144 suitable for data input. For instance, the input components 144 may include a mouse, a keyboard, a trackpad, a scroll wheel, a touchscreen, a microphone, a camera, a video camera, etc.

Operation of the computing system 100 is now set forth. Prior to receiving genetic test results for a genetic test for a genetic condition that a patient has undergone, the genetic test results ingestion application 108 receives a plurality of genetic test results for a plurality of patients that have undergone the genetic test for the genetic condition from a genetic laboratory device (or several genetic laboratory devices) in the plurality of genetic laboratory devices 122-124. Each genetic test result in the plurality of genetic test results is for the same genetic test performed by the same genetic laboratory. It is contemplated that each genetic test result in the plurality of genetic test results are in a semi-structured format; however, in the event that some or all of the genetic test results in the plurality of genetic test results are in an unstructured format, the genetic test results ingestion application 108 may apply an optical character recognition (OCR) process to each genetic test result in the plurality of genetic test results such that each genetic test result is formatted in the semi-structured format.

The genetic test results ingestion application 108 then identifies fields in the plurality of genetic test results. Each field includes a data element and a label assigned to the data element. In an example, the label may be "PATIENT NAME" and the data element may be "John Doe." In another example, the label may be "GENE SYMBOL" and the data element may be "ABO." The genetic test results ingestion application 108 then generates the set of lexing and parsing rules assigned to the genetic test performed by the genetic laboratory based upon the fields. In an example, if a field in the fields includes a label indicative of a patient name and the data element is the patient name, a regular expression to be included in the set of lexing and parsing rules for the genetic test may be "/PATIENT_NAME: (\w) */". This regular expression indicates that a series of letters after a "PATIENT_NAME:" text in the genetic test results is to be regarded as a name of the patient (and included in processed genetic test results).

In an embodiment, the genetic test results ingestion application 108 may identify the fields using a computer-implemented machine learning model. In another embodiment, the genetic test results ingestion application 108 may be employed by a user in order to generate and validate the set of lexing and parsing rules. In yet another embodiment, the genetic test results ingestion application 108 may utilize an external genetic data repository to generate the set of lexing and parsing rules for the genetic test, wherein the external genetic data repository includes lists of genes tested for in different genetic tests as well as their clinical significance.

In an embodiment, the genetic test results ingestion application 108 may extract text blocks from each genetic test result in the plurality of genetic test results. The genetic test results ingestion application 108 may record locations of the text blocks (e.g., coordinates on a page) and formatting of the text blocks (e.g., font, font size, bold, italics, etc.). The genetic test results ingestion application 108 may also mark the text blocks into paragraphs and tables. The genetic test results ingestion application 108 may additionally mark paragraph headers, table column headers, and table row headers. The set of lexing and parsing rules may further be generated based upon the text blocks.

In an embodiment, the genetic test results ingestion application 108 may group fields in the fields according to whether or not the fields are expected multiple times within the genetic test results. In an example, fields relating to a patient medical record number, a patient first name, a patient last name, a patient gender, a patient date of birth, a genetic laboratory name, a specimen name, a method of collecting the specimen, results, and/or an interpretation of the results are expected to occur once in the genetic test results and hence are grouped together. In another example, fields relating to identifiers for genes and/or identifiers for alterations of genes are expected to occur multiple times within genetic test results and hence are grouped together. The set of lexing and parsing rules may further be generated based upon groupings of the fields.

Subsequent to generating the set of lexing and parsing rules for the genetic test performed by the genetic laboratory, the genetic test results ingestion application 108 may validate the set of lexing and parsing rules against additional genetic test results of the same type in order to verify that the set of lexing and parsing rules properly identifies labels and their assigned data elements in the additional genetic test results.

Subsequently, it is contemplated that a patient undergoes the genetic test for a genetic condition and that genetic test results for the genetic test are available. As such, the genetic test results ingestion application 108 receives genetic test results for the patient from a genetic laboratory device in the plurality of genetic laboratory devices 122-124. The genetic laboratory device is under control of the genetic laboratory that performed the genetic test. The genetic test results for the patient may be formatted in an unstructured format, a semi-structured format, or a structured format (described above). The genetic test results ingestion application 108 also receives an identifier for the genetic laboratory and an identifier for the genetic test from the genetic laboratory device. In an embodiment, the identifier for the genetic laboratory and the identifier for the genetic test are comprised by the genetic test results. In another embodiment, the identifier for the genetic laboratory and the identifier for the genetic test are received separately from the genetic test results.

Responsive to receiving the genetic test results, the genetic test results ingestion application 108 identifies whether the genetic test results are formatted in the unstructured format, the semi-structured format, or the structured format. More specifically, the genetic test results ingestion application 108 may read a file extension of the genetic test results and may identify the genetic test results as being formatted in the unstructured format, the semi-structured format, or the structured format based upon the file extension.

When the genetic test results ingestion application 108 identifies the genetic test results as being formatted in the unstructured format, the genetic test results ingestion application 108 performs an OCR process on the genetic test results such that the genetic test results are formatted in the semi-structured format. More specifically, the genetic test results ingestion application 108 may utilize the OCR process to read pixels in the (unstructured) genetic test results that are indicative of text and generate computer-readable text based upon the pixels. In a specific example, when the format type of the (unstructured) genetic test results is a JPEG, the genetic test results ingestion application 108 may apply the OCR process to the genetic test results to output a searchable PDF or a text file (i.e., a semi-structured format).

When the genetic test results ingestion application 108 identifies the genetic test results as being formatted in the semi-structured format (or the genetic test results ingestion application 108 has performed the OCR process such that the genetic test results are formatted in the semi-structured format), the genetic test results ingestion application 108 identifies a set of lexing and parsing rules assigned to the genetic test performed by the genetic laboratory by executing a search over the sets of lexing and parsing rules 118 based upon the identifier for the genetic test and the identifier for the genetic laboratory. The search produces search results, wherein the search results include the set of lexing and parsing rules assigned to the genetic test performed by the genetic laboratory. The genetic test results ingestion application 108 identifies the set of lexing and parsing rules based upon the search results.

The genetic test results ingestion application 108 then generates processed genetic test results by applying the set of lexing and parsing rules to the (semi-structured) genetic test results for the patient. The processed genetic test results may include an identifier for the patient, identifiers for one or more genetic variations for which the patient was tested, and an indication as to whether the patient has the one or more genetic variations. In an embodiment, the processed genetic test results may be formatted in one of the structured formats identified above. The genetic test results ingestion application 108 may then store the processed genetic test results in the data store 110 as part of the processed genetic test results 120 (or in another data store).

When the genetic test results ingestion application 108 identifies the genetic test results as being formatted in the structured format, the genetic test results ingestion application 108 may store the structured genetic test results as processed genetic test results in the processed genetic test results 120 retained in the data store 110. Alternatively, when the genetic test results are in a first structured format, but a second structured format is desired, the genetic test results ingestion application 108 may transform the structured genetic test results to the second structured format using mappings which map fields in the first structured format to fields in the second structured format. The genetic test results ingestion application 108 may store the genetic test results in the second structured format as the processed genetic test results.

Subsequently, it is contemplated that the healthcare worker 146 wishes to view the processed genetic test results for the patient. As such, the genetic test results viewer application 134 may receive input from the healthcare worker 146 indicating an intent to view the processed genetic test results. The genetic test results viewer application 134 transmits an indication of the intent to view the processed genetic test results to the genetic test results ingestion application 108. Responsive to receiving the indication, the genetic test results ingestion application 108 transmits the processed genetic test results to the genetic test results viewer application 134, whereupon the genetic test results viewer application 134 presents the processed genetic test results on the display 140 of the client computing device 128.

In an embodiment, subsequent to generating and storing the processed genetic test results, the genetic test results ingestion application 108 may purge the (original) genetic test results from the data store 110.

Although the above-described process has been described as utilizing genetic test results for a single genetic test of a patient, it is to be understood that the above-described process may be utilized for many different genetic tests performed by many different genetic laboratories for many different patients.

Figure 2:
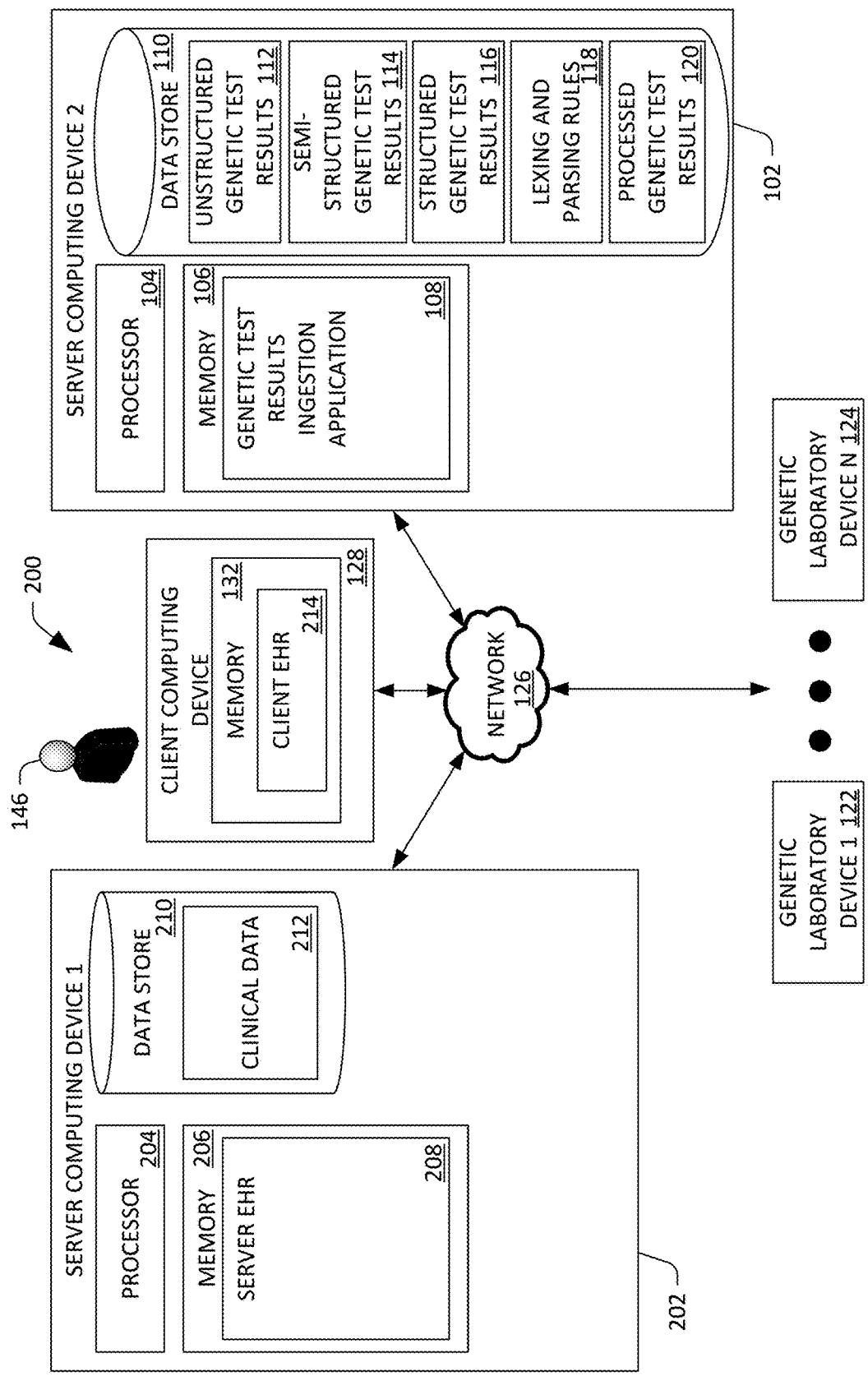
FIG. 2 is a functional block diagram of another exemplary computing system that facilitates ingesting genetic test results.

Referring now to FIG. 2, another exemplary system 200 that facilitates ingesting genetic test results is illustrated. The computing system 200 includes a first server computing device 202. The first server computing device 202 comprises a processor 204 and memory 206, wherein the memory 206 has a server electronic health records application (server EHR) 208 loaded therein. In general, the server EHR 208 is configured to perform a variety of tasks related to patient healthcare in a healthcare facility (e.g., patient intake, prescription generation, patient record creation and maintenance, etc.).

The first server computing device 202 may additionally comprise a data store 210. The data store 210 includes clinical data 212 for patients (amongst other data), wherein the clinical data 212 is maintained by the server EHR 208. The clinical data 212 may include electronic health records, prescription records, claims data, patient/disease registries, health surveys data, and/or clinical trials data.

The computing system 200 additionally comprises the server computing device 102 (referred to now as the second server computing device 102) which is in communication with the first server computing device 202 by way of the network 126 (or another network). The second server computing device 102 comprises the components described above in the description of FIG. 1.

The computing system 200 also comprises the client computing device 128 (described in the description of FIG. 1) which is in communication with the first server computing device 202 and the second server computing device 102 by way of the network 126 (or another network). The client computing device 128 comprises the components described above in the description of FIG. 1; however, in the computing system 200, the memory 132 has a client electronic health records application (client EHR) 214 loaded therein (in addition to the genetic test results viewer application 134). In general, the client EHR 214 (when executed by the processor 130) is configured to interface with the server EHR 208 executing on the first server computing device 202, thereby providing the healthcare worker 146 with access to functionality of the server EHR 208.

The computing system 200 also includes the plurality of genetic laboratory devices 122-124 described above in the description of FIG. 1.

In operation, the computing system 200 operates in a manner similar to that described above in the description of FIG. 1. However, in the computing system 200, the processed genetic test results for a patient may be viewed as part of a clinical workflow. More specifically, the genetic test results ingestion application 108 may transmit an indication to the server EHR 208 when the genetic test results ingestion application 108 receives genetic test results for a patient. The genetic test results ingestion application 108 performs the functionality described above in the description of FIG. 1 in order to generate processed genetic test results based upon the genetic test results.

Responsive to receiving the indication from the genetic test results ingestion application 108, the server EHR 208 may transmit data to the client EHR 214 causing the client EHR 214 to present a visual marker within a graphical user interface (GUI) for the client EHR 214 shown on the display 140 of the client computing device 128. The visual marker indicates that genetic test results for the patient are available.

Responsive to receiving a selection of the visual marker from the healthcare worker 146, the client EHR 214 may cause the genetic test results viewer application 134 to be launched on the client computing device 128. In an embodiment, a GUI for the genetic test results viewer application 134 may be presented on the display 140 as an overlay to the GUI for the client EHR 214. The genetic test results ingestion application 108 may transmit the processed genetic test results for the patient to the genetic test results viewer application 134, and the genetic test results viewer application 134 may present the processed genetic test results for the patient within the GUI for the genetic test results viewer application 134.

Turning now to FIG. 3, a depiction 300 of semi-structured genetic test results for a patient is illustrated. As shown in FIG. 3, the semi-structured genetic test results depict information with respect to a genetic test. For instance, the semi-structured genetic test results may include an identifier for a patient (e.g., a name) that underwent the genetic test, a date of birth of the patient, a case number for the genetic test, an identifier for the specimen from the patient used in the genetic test, a medical record number (MRN) for the patient, an identifier for the ordering physician of the genetic test, an optional identifier for an additional recipient that is to receive the genetic test results, an identifier for a pathologist, an identifier for a collection site of the sample used in the genetic test, and/or a date of the genetic test. The semi-structured genetic test results may include identifiers for genes in which genetic alterations/variations were found in the genetic tests, as well as identifiers for genes in which no genetic alterations/variations were found.

Figure 4:
FIG. 4 is a depiction of processed genetic test results generated by applying a set of lexing and parsing rules to the exemplary semi-structured genetic test results depicted in FIG. 3.

With reference to FIG. 4, a depiction 400 of processed genetic test results generated by applying a set of lexing and parsing rules to the semi-structured genetic test results depicted in FIG. 3 is illustrated.

Figure 5:
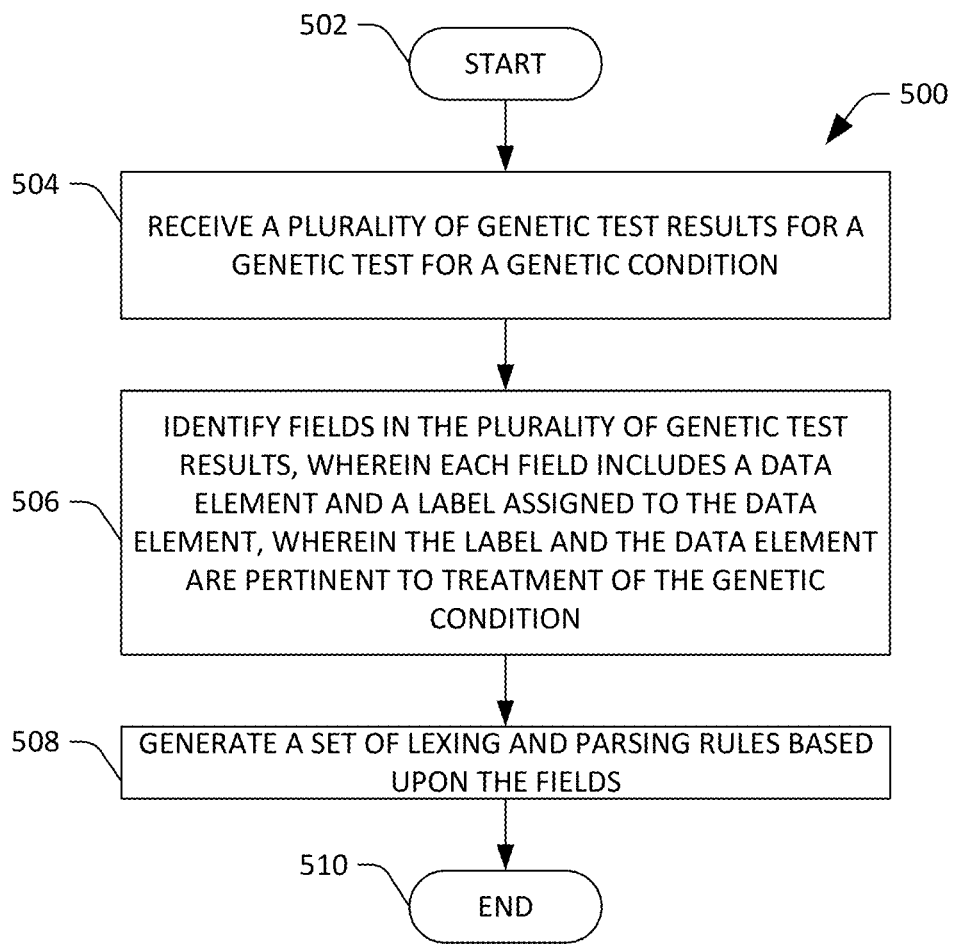
FIG. 5 is a flow diagram that illustrates an exemplary methodology executed by a server computing device for generating a set of lexing and parsing rules assigned to a genetic test performed by a genetic laboratory.
Figure 6:
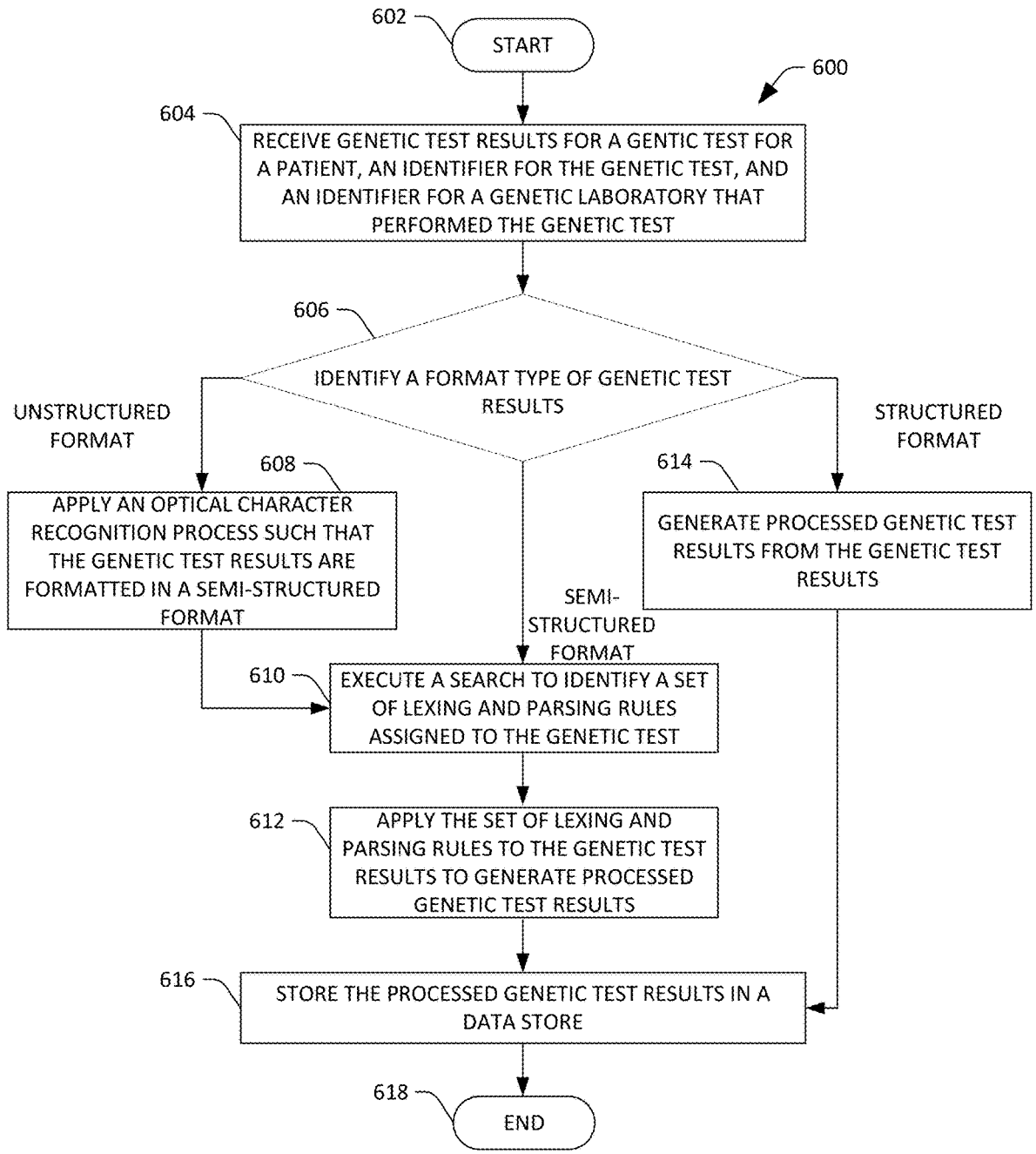
FIG. 6 is a flow diagram that illustrates an exemplary methodology executed by a server computing device for ingesting genetic test results.
Figure 7:
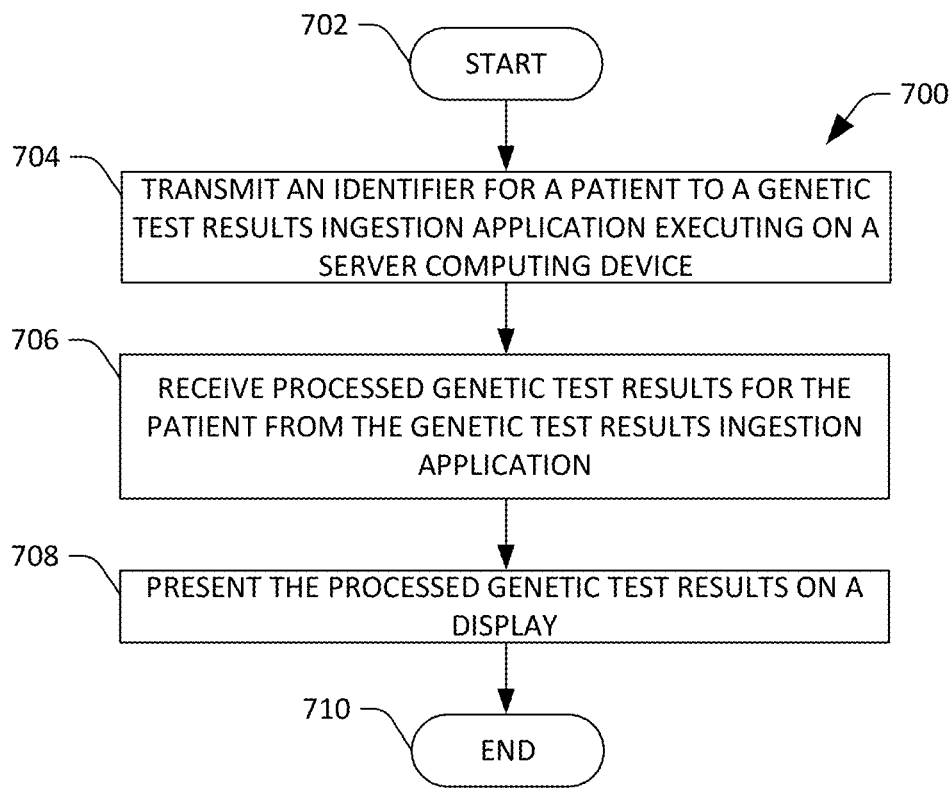
FIG. 7 is a flow diagram that illustrates an exemplary methodology executed by a client computing device for displaying processed genetic test results.

FIGS. 5-7 illustrate exemplary methodologies relating to ingesting genetic test results. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Referring now to FIG. 5, a methodology 500 performed by a genetic test results ingestion application that facilitates generating a set of lexing and parsing rules that can be utilized to generate processed genetic test results is illustrated. The methodology 500 begins at 502, and at 504 the genetic test results ingestion application receives a plurality of genetic test results for a genetic test for a genetic condition performed by a genetic laboratory. At 506, the genetic test results ingestion application identifies fields in the plurality of genetic test results. Each field includes a data element and a label assigned to the data element, wherein the data element and the label are pertinent to treatment of patients who underwent the genetic test. At 508, the genetic test results ingestion application generates a set of lexing and parsing rules for the genetic test performed by the genetic laboratory based upon the fields. The methodology 500 concludes at 510.

Referring now to FIG. 6, a methodology 600 performed by a genetic test results ingestion application that facilitates ingesting genetic test results for a patient is illustrated. The methodology 600 begins at 602, and at 604 the genetic test results ingestion application receives genetic test results for a genetic test that a patient has undergone, an identifier for the genetic test, and an identifier for a genetic laboratory that performed the genetic test from a genetic laboratory device of the genetic laboratory. The genetic test results are formatted in an unstructured format, a semi-structured format, or a structured format. At 606, the genetic test results ingestion application identifies a format type (i.e., unstructured, semi-structured, or structured) of the genetic test results.

At 608, when the genetic test results are formatted in the unstructured format, the genetic test results ingestion application applies an OCR process to the genetic test results such that the genetic test results are formatted in the semi-structured format.

At 610, when the genetic test results are formatted in the semi-structured format (either originally in the semi-structured format or in the semi-structured format as a result of the OCR process), the genetic test results ingestion application executes a search over sets of lexing and parsing rules to identify a set of regular expression assigned to the genetic test performed by the genetic laboratory. At 612, the genetic test results ingestion application applies the set of lexing and parsing rules to the genetic test results to generate processed genetic test results. For instance, the processed genetic test results may be in the structured format.

At 614, when the genetic test results are structured, the genetic test results ingestion application generates the processed genetic test results from the genetic test results.

At 616, the genetic test results ingestion application stores the processed genetic test results in a data store. The methodology 600 concludes at 618.

Referring now to FIG. 7, a methodology 700 performed by a genetic test results viewer application executing on a client computing device that facilitates displaying processed genetic test results for a patient is illustrated. The methodology 700 begins at 702, and at 704 the genetic test results viewer application transmits an identifier for a patient to a genetic test results ingestion application executing on a server computing device that is in network communication with the client computing device. The genetic test results ingestion application retrieves the processed genetic test results for the patient based upon the identifier for the patient and transmits the processed genetic test results to the genetic test results viewer application. At 706, the genetic test results viewer application receives processed genetic test results for the patient from the genetic test results ingestion application. At 708, the genetic test results viewer application presents the processed genetic test results on a display of the client computing device. The methodology 700 concludes at 710.

Figure 8:
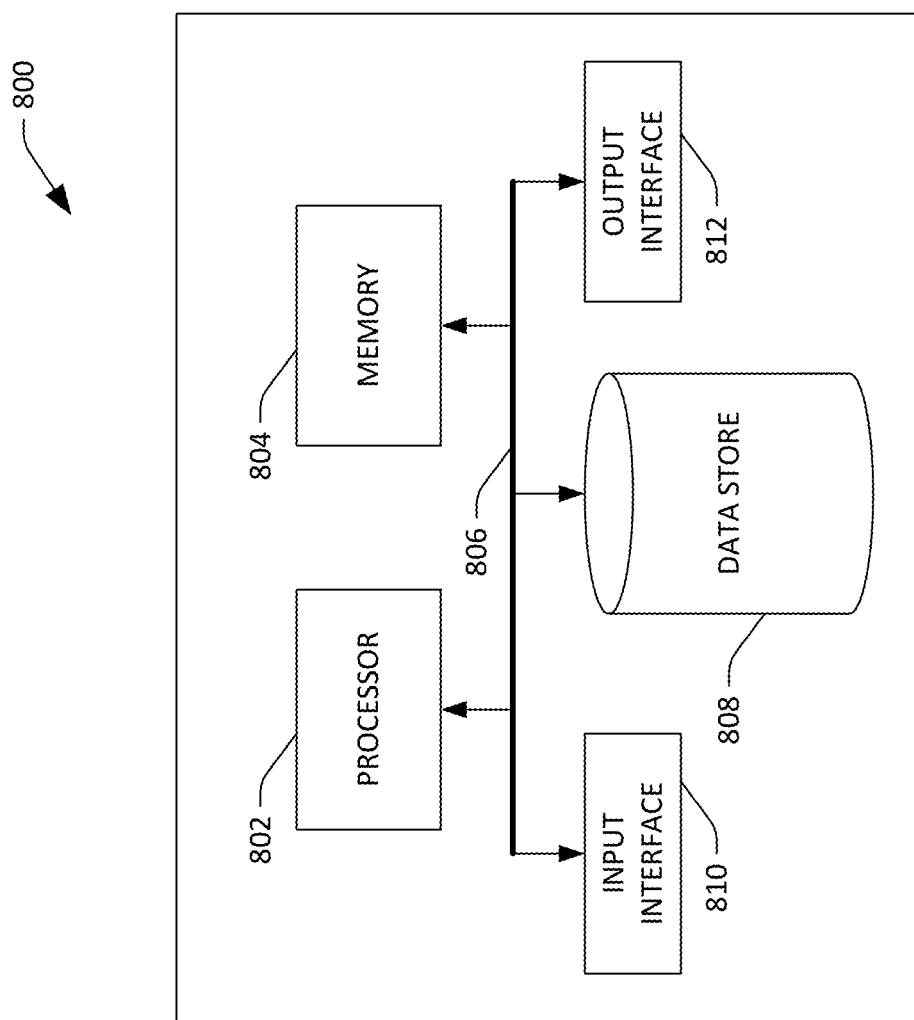
FIG. 8 is an exemplary computing system.

Referring now to FIG. 8, a high-level illustration of an exemplary computing device 800 that can be used in accordance with the systems and methodologies disclosed herein is illustrated. For instance, the computing device 800 may be used in a system that ingests genetic test results. By way of another example, the computing device 800 can be used in a system that displays processed genetic test results. The computing device 800 includes at least one processor 802 that executes instructions that are stored in a memory 804. The instructions may be, for instance, instructions for implementing functionality described as being carried out by one or more components discussed above or instructions for implementing one or more of the methods described above. The processor 802 may access the memory 804 by way of a system bus 806. In addition to storing executable instructions, the memory 804 may also store clinical data, unstructured genetic test results, semi-structured genetic test results, structured genetic test results, processed genetic test results, sets of lexing and parsing rules, etc.

The computing device 800 additionally includes a data store 808 that is accessible by the processor 802 by way of the system bus 806. The data store 808 may include executable instructions, clinical data, unstructured genetic test results, semi-structured genetic test results, structured genetic test results, processed genetic test results, sets of lexing and parsing rules, etc. The computing device 800 also includes an input interface 810 that allows external devices to communicate with the computing device 800. For instance, the input interface 810 may be used to receive instructions from an external computer device, from a user, etc. The computing device 800 also includes an output interface 812 that interfaces the computing device 800 with one or more external devices. For example, the computing device 800 may display text, images, etc. by way of the output interface 812.

It is contemplated that the external devices that communicate with the computing device 800 via the input interface 810 and the output interface 812 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 800 in a manner free from constraints imposed by input devices such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 800 may be a distributed system. Thus, for instance, several devices may be in communication by way of a network connection and may collectively perform tasks described as being performed by the computing device 800.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to store desired program code in the form of instructions or data structures and that can be accessed by a computer. Disk and disc, as used herein, include compact disc (CD), laser disc, optical disc, digital versatile disc (DVD), floppy disk, and blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. A server computing device comprising:
    a processor; and
    memory storing a genetic test results ingestion application, wherein the genetic test results ingestion application is configured to cause, when executed by the processor, the processor to perform acts comprising:
        receiving, from a genetic laboratory device of a genetic laboratory, 1) genetic test results for a genetic test a patient has undergone, 2) an identifier for the genetic test, and 3) an identifier for the genetic laboratory that performed the genetic test, wherein the genetic test results are formatted in:
            an unstructured format such that the genetic test results fail to include computer-readable text;
            a semi-structured format such that the genetic test results include the computer-readable text; or
            a structured format such that the genetic test results include the computer-readable text and utilize standardized labels for data elements in the genetic test results;
        identifying whether the genetic test results are formatted in the unstructured format, the semi-structured format, or the structured format;
        when the genetic test results are identified as being formatted in the semi-structured format:
        executing a search over sets of lexing and parsing rules retained in a data store, wherein the data store is included in the server computing device or in network communication with the server computing device, wherein the search is based upon the identifier for the genetic test and the identifier for the genetic laboratory, and further wherein the sets of lexing and parsing rules comprise a set of lexing and parsing rules that is assigned to a combination of the genetic test and the genetic laboratory;
        identifying, based upon the search, the set of lexing and parsing rules that is assigned to the combination of the genetic test and the genetic laboratory; and
        generating processed genetic test results for the genetic test results by applying the set of lexing and parsing rules to the genetic test results, wherein the processed genetic test results are formatted in the structured format.

2. The server computing device of claim 1, the acts further comprising:
    when the genetic test results are identified as being formatted in the unstructured format:

applying an optical character recognition (OCR) process to the genetic test results such that the genetic test results are formatted in the semi-structured format.

3. The server computing device of claim 1, wherein the structured format is one of Health Level Seven International (HL7), clinical document architecture (CDA), consolidated clinical document architecture (CCDA), or a comma-separated values (CSV).

4. The server computing device of claim 1, wherein the unstructured format is one of a non-searchable portable document format (PDF), a facsimile, a joint photographic experts group (JPEG), a JPEG file interchange format (JFIF), a tagged imaged file format (TIFF), a graphics interchange format (GIF), a windows bitmap (BMP), or a portable network graphics (PNG).

5. The server computing device of claim 1, wherein the genetic test results include a file extension, wherein identifying whether the genetic test results are formatted in the unstructured format, the semi-structured format, or the structured format comprises:
  reading the file extension of the genetic test results; and
  identifying the genetic test results as being formatted in the unstructured format, the semi-structured format, or the structured format based upon the file extension.

6. The server computing device of claim 1, the acts further comprising:
  prior to receiving the genetic test results for the patient from the genetic laboratory device, generating the set of lexing and parsing rules.

7. The server computing device of claim 1, the acts further comprising:
  transmitting the processed genetic test results to a client computing device that is in network communication with the server computing device, wherein the client computing device presents the processed genetic test results on a display of the client computing device.

8. The server computing device of claim 1, wherein the semi-structured format is a searchable portable document format (PDF), a text file, or a Hypertext Markup Language (HTML) file.

9. The server computing device of claim 1, wherein the identifier for the genetic test and the identifier for the genetic laboratory are comprised by the genetic test results.

10. The server computing device of claim 1, the acts further comprising:
  when the genetic test results are identified as being formatted in the structured format:
    storing the genetic test results in the data store as the processed genetic test results.

11. A computer-readable storage medium comprising a genetic test results ingestion application that is configured to cause, when executed by a processor of a server computing device, the processor to perform acts comprising:
  receiving, from a genetic laboratory device of a genetic laboratory, 1) genetic test results for a genetic test a patient has undergone, 2) an identifier for the genetic test, and 3) an identifier for the genetic laboratory that performed the genetic test, wherein the genetic test results are formatted in:
    an unstructured format such that the genetic test results fail to include computer-readable text;
    a semi-structured format such that the genetic test results include the computer-readable text; or
    a structured format such that the genetic test results include the computer-readable text and utilize standardized labels for data elements in the genetic test results;
  identifying that the genetic test results are formatted in the unstructured format;
  upon identifying that the genetic test results are formatted in the unstructured format, applying an optical character recognition (OCR) process to the genetic test results such that the genetic test results are formatted in the semi-structured format;
  upon the OCR process being applied to the genetic test results, identifying a set of lexing and parsing rules from amongst several sets of lexing and parsing rules retained in a data store, wherein the set of lexing and parsing rules is assigned to a combination of the genetic test and the genetic laboratory, and further wherein the set of lexing and parsing rules is identified based upon the identifier for the genetic test and the identifier for the genetic laboratory;
  generating processed genetic test results for the genetic test results by applying the set of lexing and parsing rules to the genetic test results, wherein the processed genetic test results are formatted in the structured format; and
  storing the processed genetic test results in the data store.

12. The computer-readable storage medium of claim 11, wherein the unstructured format is an image file format.

* * * * *